(12) United States Patent
Mooijman et al.

(10) Patent No.: US 7,044,515 B2
(45) Date of Patent: May 16, 2006

(54) BUMPER BEAM WITH CRUSH CANS

(75) Inventors: Frank Mooijman, Halsteren (NL); Dominic McMahon, Bergen op Zoom (NL); Srikanth M. Santhanam, Windsor (CA)

(73) Assignee: General Electric Company, Schenectady, NY (US)

( * ) Notice: Subject to any disclaimer, the term of this patent is extended or adjusted under 35 U.S.C. 154(b) by 613 days.

(21) Appl. No.: 10/221,433

(22) PCT Filed: Sep. 12, 2001

(86) PCT No.: PCT/US01/28583

§ 371 (c)(1),
(2), (4) Date: Sep. 10, 2002

(87) PCT Pub. No.: WO03/022640

PCT Pub. Date: Mar. 20, 2003

(65) Prior Publication Data

US 2003/0050619 A1   Mar. 13, 2003

(51) Int. Cl.
*B60R 19/03* (2006.01)

(52) U.S. Cl. .................. 293/120; 293/102; 293/132; 293/133

(58) Field of Classification Search ............ 293/102, 293/120, 132, 133
See application file for complete search history.

(56) References Cited

U.S. PATENT DOCUMENTS

| 3,897,095 A | 7/1975 | Glance et al. |
| 4,951,986 A | 8/1990 | Hanafusa et al. |
| 5,988,713 A | 11/1999 | Okamura et al. |
| 6,082,792 A | 7/2000 | Evans et al. |
| 6,099,055 A | 8/2000 | Hirota et al. |
| 6,299,226 B1 | 10/2001 | Kröning et al. |

FOREIGN PATENT DOCUMENTS

GB   2134858   6/1984

*Primary Examiner*—Lori L. Coletta
(74) *Attorney, Agent, or Firm*—Armstrong Teasdale LLP

(57) ABSTRACT

A bumper assembly (10) for an automotive vehicle is described. In an example embodiment, the assembly comprises a beam and a fascia at least partially covering the beam. The beam comprises at least one crush can (12).

20 Claims, 3 Drawing Sheets

BUMPER BEAM WITH CRUSH CANS

CROSS REFERENCE TO RELATED APPLICATIONS

This application claims the benefit of International Application No. PCT/US01/28583 filed Sep. 12, 2001.

BACKGROUND OF THE INVENTION

This invention relates generally to bumpers and, more particularly, to bumper beams.

Bumpers typically extend widthwise across the front and rear of a vehicle and are mounted to rails that extend in a lengthwise direction. A typical bumper includes a steel beam or reinforcing member attached to vehicle rails and covered by a fascia. Such steel beams are heavy and typically deform, or buckle, on impact. Energy from an impact therefore may be transferred to the vehicle rails and result in additional damage to the vehicle.

Energy absorbing bumper systems attempt to reduce vehicle damage as a result of a collision by managing impact energy and intrusion while not exceeding a rail load limit of the vehicle. The efficiency of a bumper system is defined as the amount of energy absorbed over distance. A high efficiency bumper system absorbs more energy over a shorter distance than a low efficiency bumper system. High efficiency is achieved by building load quickly to just under the rail load limit and maintaining that load constant until the impact energy has been dissipated.

Some known energy absorbing bumper systems include a beam and an energy absorber coupled to the beam. The energy absorber is effective in absorbing energy from an impact. Separately fabricating an energy absorber and assembling the energy absorber to the beam increases both the fabrication and assembly costs of a bumper assembly as compared to a simple steel beam bumper.

Other known energy absorbing bumper systems utilize a foam resin, such as described in U.S. Pat. No. 4,762,352 and U.S. Pat. No. 4,941,701. Foam based systems typically have slow loading upon impact, which results in a high displacement. Further, foams are effective to a sixty or seventy percent compression, and beyond that point, foams become incompressible so that the impact energy is not fully absorbed. The remaining impact energy is absorbed through deformation of a backup beam and/or vehicle structure. Foams are also temperature sensitive so that displacement and impact absorption behavior can change substantially with temperature. Typically, as temperature is lowered, foam becomes more rigid, resulting in higher loads. Conversely, as temperature rises, foams become more compliant resulting in higher displacements and possible vehicle damage.

Still other known bumper systems include crash cans. The crash cans are separately fabricated and attached directly to a beam in alignment with the vehicle rails. The crash cans absorb energy during impact, e.g., an offset impact, and facilitate preventing damage to the beam. Separately fabricating and attaching the crash cans to the beam, however, increases bumper assembly costs and complexity.

BRIEF SUMMARY OF THE INVENTION

In one aspect, a bumper assembly for an automotive vehicle is provided. The bumper assembly comprises a beam and a fascia at least partially covering the beam. The beam comprises at least one crush can.

In another aspect, an energy absorbing beam for a bumper assembly is provided. The beam comprises a frame and a body extending from the frame. The body comprises a first transverse wall, a second transverse wall spaced from the first wall, and at least one crush can between the first and second walls.

DETAILED DESCRIPTION OF THE INVENTION

Figure 1:
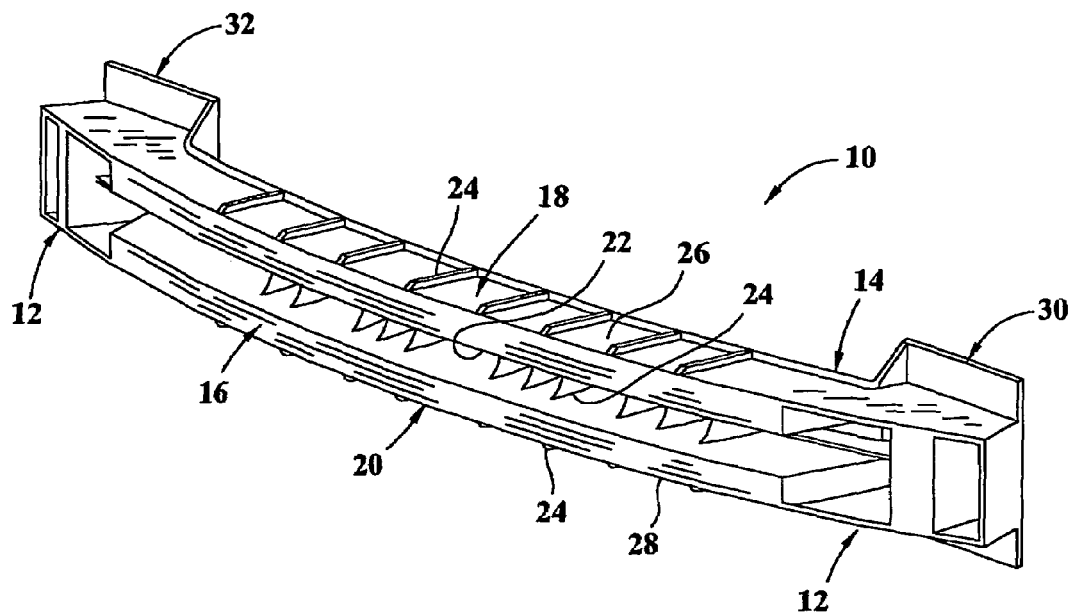
FIG. 1 is a perspective front view of a bumper beam.

A thermoplastic bumper beam that includes tunable crush cans is described below in detail. The term tunable, as used herein, means that characteristics, e.g., wall angles, of the crush cans can be selected to provide a desired operating result, as described below in more detail. The crush cans are sometimes described herein as being integral with the beam, which means that the crush cans are formed as a component of, and not separately from, the beam, which results in a one-piece unitary structure for the beam. The term integral also includes constructions in which the beam is molded in segments, and then the segments are secured together, e.g., welded.

Combining the crush cans with the beam results in a bumper system that absorbs energy without necessitating a separate energy absorber attached to the beam. For example, impact forces during low speed impacts are maintained just below a predetermined level by deforming the beam until the kinetic energy of the impact event has been absorbed. When the low speed impact is over, the beam returns substantially to its original shape and retains sufficient integrity to withstand subsequent impacts.

Further, combining the efficient energy absorbing properties of a thermoplastic beam with the integrated crush cans is believed to provide improved impact absorbing performance over traditional metal beams. In addition, the thermoplastic beam with integrated crush cans is believed to provide more efficient impact absorption than thermoplastic beams that do not include crush cans.

The bumper beam can be fabricated from one of many plastic materials including, for example, Xenoy® material which is commercially available from General Electric Company, Pittsfield, Mass. The beam is not limited to practice with such material and other materials can be used.

More specifically, the characteristics of the material utilized to form the beam include high toughness/ductility, thermally stable, high energy absorption capacity, a good modulus-to-elongation ratio and recyclability. While the beam may be molded in segments, the beam also can be of unitary construction made from a tough plastic material. An example material for the beam is Xenoy material, as referenced above. Of course, other engineered thermoplastic resins can be used. Typical engineering thermoplastic resins include, but are not limited to, acrylonitrile-butadiene-styrene (ABS), polycarbonate, polycarbonate/ABS blend, a copolycarbonate-polyester, acrylic-styrene-acrylonitrile (ASA), acrylonitrile-(ethylene-polypropylene diamine modified)-styrene (AES), phenylene ether resins, blends of polyphenylene ether/polyamide (NORYL GTX® from General Electric Company), blends of polycarbonate/PET/PBT, polybutylene terephthalate and impact modifier (XENOY® resin from General Electric Company), polyamides, phenylene sulfide resins, polyvinyl chloride PVC, high impact polystyrene (HIPS), low/high density polyethylene (l/hdpe), polypropylene (pp) and thermoplastic olefins (tpo). The beam also could, for example be fabricated (e.g., compression molded) from a glass mat thermoplastic (GMT), such as Azdel® material (commercially available from Azdel, Inc., Shelby, N.C. and described in U.S. Pat. No. 5,643,989).

Figure 2:
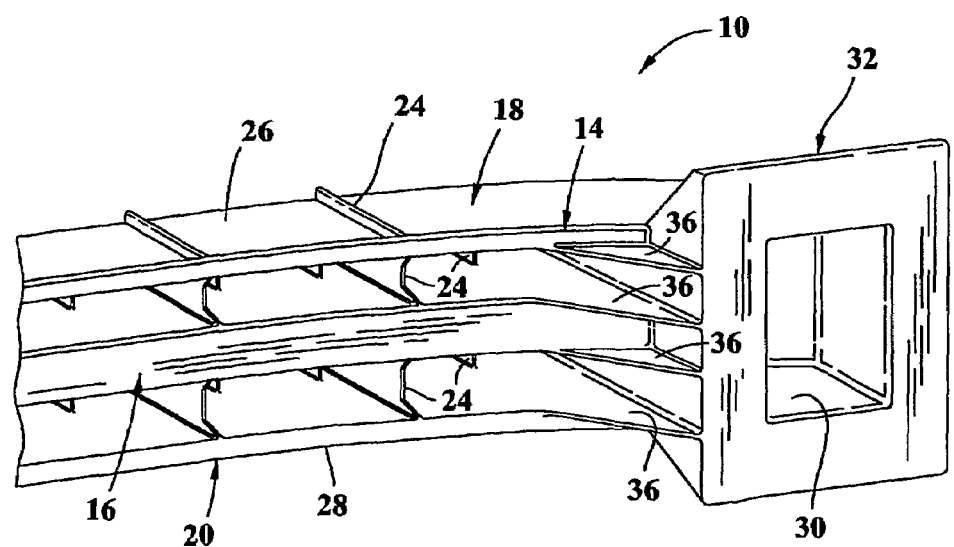
FIG. 2 is a perspective rear view of a portion of the bumper beam shown in FIG. 1.

Referring now specifically to the drawings, FIGS. 1 and 2 are a front perspective view of a bumper 10 including integral tunable crush cans 12 and a rear view of a portion of bumper 10, respectively. A fascia (not shown) ordinarily would be secured to beam 10 and typically is formed from a thermoplastic material which is amenable to finishing utilizing conventional vehicle painting and/or coating techniques. The fascia envelopes beam 10 such that beam 10 is not visible once attached to the vehicle.

Beam 10 has a generally rectangular cross sectional shape and includes a frame 14. A body 16 that extends from frame 14 includes first and second longitudinally extending flanges 18 and 20. Flanges 18 and 20 define a channel 22 that also extends longitudinally. A plurality of reinforcing and stiffening ribs 24 are positioned between flanges 18 and 20 in channel 22, and also on exterior surfaces 26 and 28 of flanges 18 and 20.

Beam 10 also includes vehicle attachment portions 30, 32, and includes openings 34 for securing beam 10 to the frame rails of the vehicle. Reinforcing members 36 extend from body 16 to attachment portion 32. Crush cans 12 generally are located in alignment with the vehicle rails when bumper 10 is secured to a vehicle. By positioning crush cans 12 in alignment with the vehicle rails, such crush cans operate to facilitate reducing damage to the vehicle during an impact.

Figure 3:
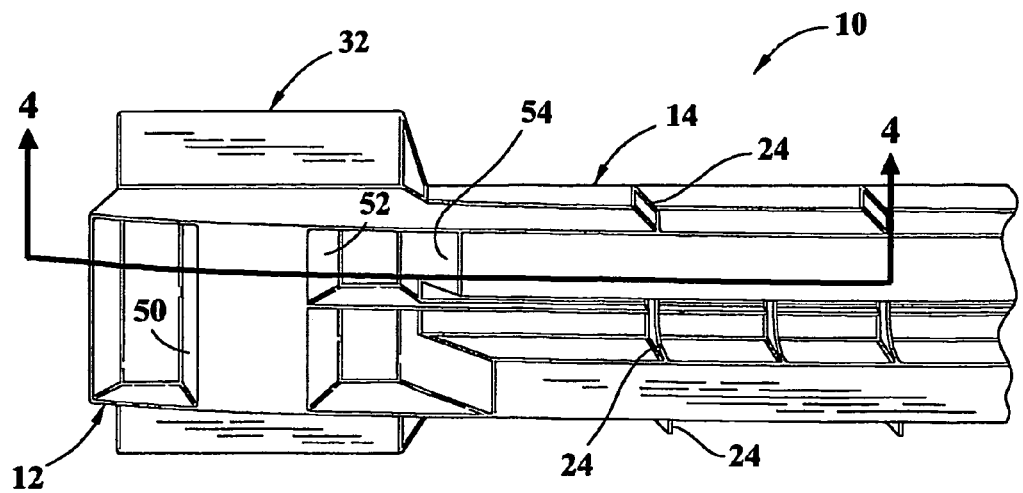
FIG. 3 is a perspective front view of a portion of the bumper beam shown in FIG. 1.
Figure 4:
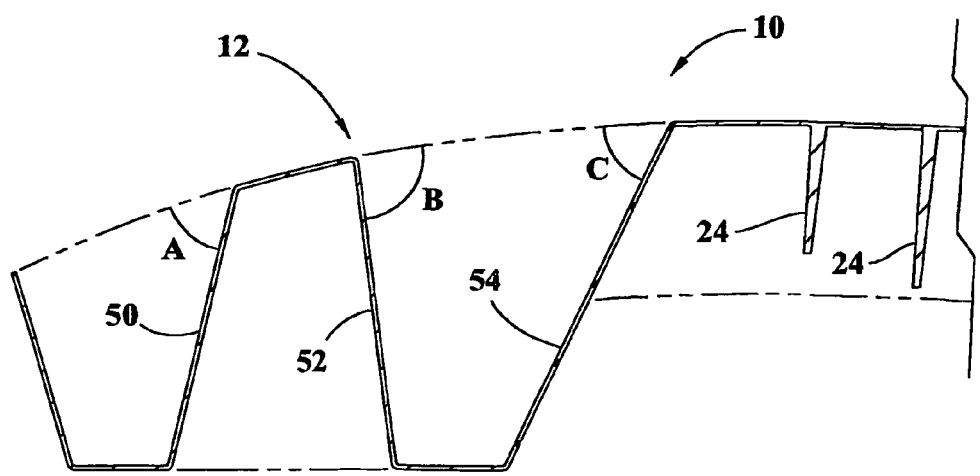
FIGS. 4, 5, and 6 are cross-sectional views through line 4—4 in FIG. 3 and showing different crush can wall configurations.
Figure 5:
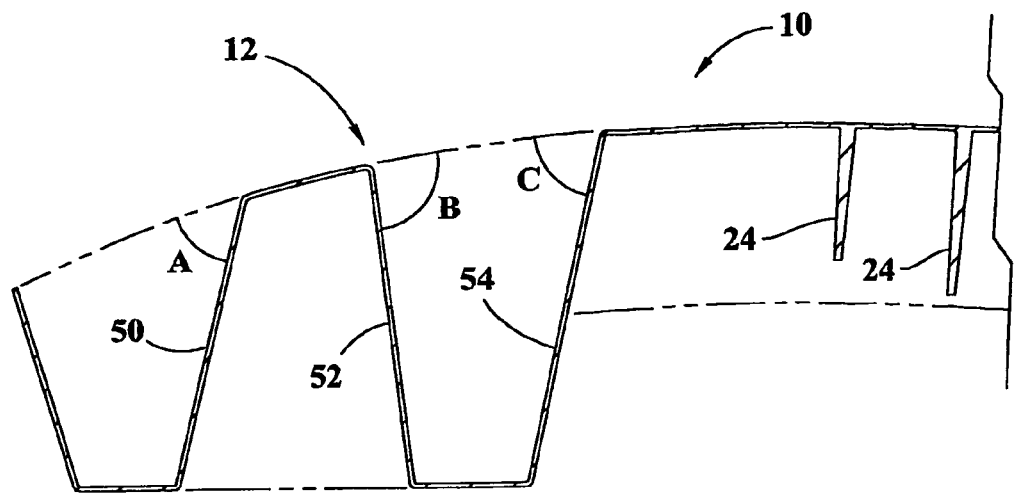
Figure 6:
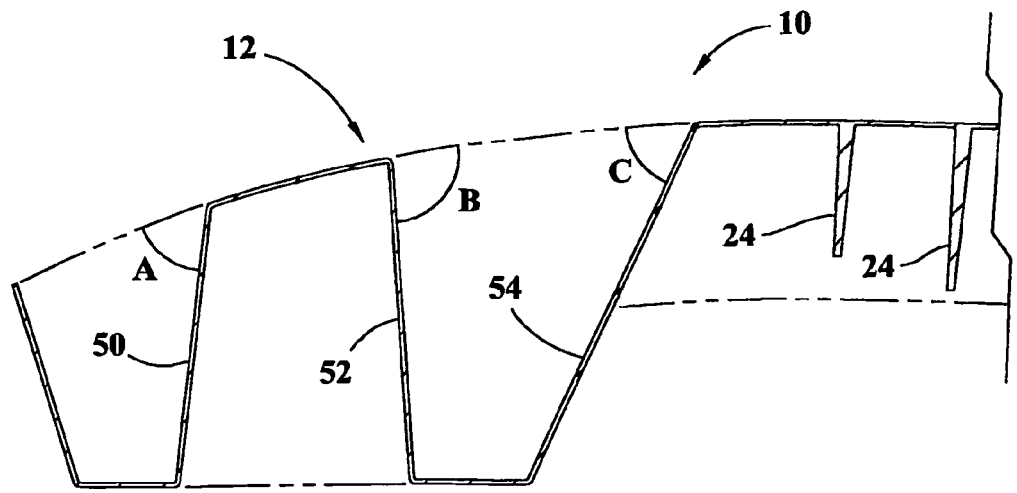

Referring to FIG. 3, which is a perspective front view of a portion of bumper 10, crush can 12 includes a plurality of walls 50, 52, 54. Also, and referring to FIGS. 4, 5 and 6, which are cross sectional views through line 4—4 in FIG. 3 and illustrate alternative crush angles A, B, C, varying crush angles A, B, C results in different stiffness and impact characteristics. For example, by changing walls 50, 52, 54 to be more upright, crush can 12 is more stiff. Also, positioning walls 50, 52, 54 closer together results in increasing the stiffness of crush can 12. In addition, spacing of ribs 24 can be altered, i.e., beam 10 becomes more stiff as ribs 24 are spaced closer together.

By varying at least the wall angles A, B, C, the spacing of walls 50, 52, 54, and the spacing of ribs 24, crush can 12 is tunable to provide a desired stiffness. Since vehicles have different weights and operating applications (e.g., non-commercial passenger vehicle, commercial passenger vehicle, light truck), bumper 10 can be tuned for a particular vehicle weight and application.

Of course, other variables can be used to for tuning crush cans 12. For example, crush can 12 can also be tailored for specific applications by varying the wall thickness of walls 50, 52, 54. For example, the nominal thickness of the walls may broadly range from about 1.75 mm to about 3.0 mm. More specifically, for certain low impact applications the nominal wall thickness may generally range from about 1.75 mm to about 2.0 mm and for other applications the walls would more likely be in the range of about 2.5 mm to 3.0 mm.

Another aspect in appropriately tuning crush cans 12 is the selection of the thermoplastic resin to be employed. The resin employed may be a low modulus, medium modulus or high modulus material as needed. By carefully considering each of these variables, crush cans 12 can meet the desired energy impact objectives.

As explained above, integrating crush cans with an injection molded thermoplastic beam is believed to provide enhanced energy absorption efficiency over steel beams and simple thermoplastic beams. Enhanced impact performance translates to reduced costs of repair for low speed "fender benders" and reduced vehicle damage during higher speed collisions. Further, since a separate energy absorber is not utilized, cost savings also are believed to be achieved with such a bumper beam configuration. The combination of the thermoplastic beam and the tunable crush cans provides an efficient, fast loading and controlled impact event.

While the invention has been described in terms of various specific embodiments, those skilled in the art will recognize that the invention can be practiced with modification within the spirit and scope of the claims.

What is claimed is:

1. A bumper assembly comprising:
   a beam comprising:
      at least one crush can;
      a first channel comprising an upper traverse wall, a lower traverse wall, and an outer wall;
      a second channel comprising an upper traverse wall, a lower traverse wall, and an outer wall; and
      a back wall extending between said lower traverse wall of said first channel and said upper traverse wall of said second channel;
      said back wall, said lower traverse wall of said first channel, and said upper traverse wall of said second channel defining a third channel located between said first channel and said second channel; and
   a fascia for covering at least a portion of said beam.

2. A bumper assembly according to claim 1 wherein said beam comprises a thermoplastic.

3. A bumper assembly according to claim 1 wherein said beam comprises a unitary elongated thermoplastic body.

4. A bumper assembly according to claim 1 wherein said crush can is tunable.

5. A bumper assembly according to claim 1 wherein said beam further comprises a frame.

6. A bumper assembly according to claim 1 wherein a first crush can is configured to align with a first vehicle rail, and a second crush can is configured to align with a second vehicle rail.

7. A bumper assembly according to claim 1 wherein said crush can comprises a plurality of spaced walls, and wherein at least one of wall spacing, wall angles, wall thickness, and wall material is selectable.

8. An energy absorbing beam for a vehicle, said beam comprising a frame and a body extending from said frame, said body comprising:
   a first channel comprising an upper traverse wall, a lower traverse wall, and an outer wall;
   a second channel comprising an upper traverse wall, a lower traverse wall, and an outer wall; and
   a back wall extending between said lower traverse wall of said first channel and said upper traverse wall of said second channel;
   said back wall, said lower traverse wall of said first channel, and said upper traverse wall of said second channel defining a third channel located between said first channel and said second channel; and
   at least one crush can.

9. An energy absorbing beam according to claim 8 further comprising a first vehicle rail attachment portion and a second vehicle rail attachment portion, each of said vehicle rail attachment portions configured to align and secure to a respective vehicle rail.

10. An energy absorbing beam according to claim 9 wherein said beam comprises a thermoplastic.

11. An energy absorbing beam according to claim 9 wherein said beam comprises a unitary elongated thermoplastic body.

12. An energy absorbing beam according to claim 9 wherein said crush can is tunable.

13. An energy absorbing beam according to claim 9 wherein said crush can comprises a plurality of spaced walls, and wherein at least one of wall spacing, wall angles, wall thickness, and wall material is selectable.

14. A molded plastic beam for a vehicle, said beam comprising:
    at least one crush can;
    a first channel comprising an upper traverse wall, a lower traverse wall, and an outer wall;
    a second channel comprising an upper traverse wall, a lower traverse wall, and an outer wall; and
    a back wall extending between said lower traverse wall of said first channel and said upper traverse wall of said second channel;
    said back wall, said lower traverse wall of said first channel, and said upper traverse wall of said second channel defining a third channel located between said first channel and said second channel.

15. A beam according to claim 14 further comprising a frame and a body extending from said frame, said body comprising a first and a second flange, with a channel between said first and second flanges.

16. A beam according to claim 14 wherein a first crush can is configured to align with a first vehicle rail, and a second crush can is configured to align with a second vehicle rail.

17. A beam according to claim 14 wherein said beam comprises a thermoplastic.

18. A beam according to claim 14 wherein said beam comprises a unitary elongated thermoplastic body.

19. A beam according to claim 14 wherein said crush can is tunable.

20. A beam according to claim 14 wherein said crush can comprises a plurality of spaced walls, and wherein at least one of wall spacing, wall angles, wall thickness, and wall material is selectable.

* * * * *